United States Patent
Rajek

(10) Patent No.: US 9,820,774 B2
(45) Date of Patent: Nov. 21, 2017

(54) ORTHOPEDIC TRIGGER APPARATUS

(71) Applicant: Bradshaw Medical, Inc., Kenosha, WI (US)

(72) Inventor: Andrew Rajek, Cudahy, WI (US)

(73) Assignee: BRADSHAW MEDICAL, INC., Kenosha, WI (US)

(*) Notice: Subject to any disclaimer, the term of this patent is extended or adjusted under 35 U.S.C. 154(b) by 315 days.

(21) Appl. No.: 14/851,594

(22) Filed: Sep. 11, 2015

(65) Prior Publication Data
US 2017/0042574 A1    Feb. 16, 2017

Related U.S. Application Data

(60) Provisional application No. 62/204,189, filed on Aug. 12, 2015.

(51) Int. Cl.
| A61B 17/56 | (2006.01) |
|---|---|
| A61B 17/28 | (2006.01) |
| A61B 17/00 | (2006.01) |

(52) U.S. Cl.
CPC .............. *A61B 17/56* (2013.01); *A61B 17/28* (2013.01); *A61B 2017/00407* (2013.01)

(58) Field of Classification Search
CPC ................ A61B 17/56; A61B 17/28; A61B 2017/00407
See application file for complete search history.

(56) References Cited

U.S. PATENT DOCUMENTS

| 6,790,209 B2* | 9/2004 | Beale ................ A61B 17/7032 606/104 |
| 7,611,517 B2* | 11/2009 | Lim .................... A61B 17/7086 606/86 A |
| 8,235,997 B2 | 8/2012 | Hoffman et al. |
| 9,622,732 B2* | 4/2017 | Martinelli ............ A61B 17/025 |
| 2006/0079912 A1* | 4/2006 | Whitfield .............. A61B 17/10 606/142 |
| 2007/0093856 A1* | 4/2007 | Whitfield ........... A61B 17/1285 606/142 |
| 2008/0262318 A1* | 10/2008 | Gorek ................ A61B 17/0206 600/235 |
| 2009/0203969 A1* | 8/2009 | Cohen .................... A61B 17/02 600/245 |

(Continued)

*Primary Examiner* — Christian Sevilla
(74) *Attorney, Agent, or Firm* — Ryan Kromholz & Manion, S.C.

(57) ABSTRACT

The present invention is an orthopedic trigger apparatus including a rack assembly, a trigger housing assembly and a trigger assembly. The rack assembly includes a linear rack rotatably connected to a first handle of an orthopedic instrument. The trigger housing assembly includes a trigger housing connected to a second handle of the orthopedic instrument, with a rack engagement cylinder and a spring enclosed within the trigger housing. The rack engagement cylinder includes a toothed rack. The spring contacts a second surface of the toothed rack stop, biasing a first pawled surface into meshing with the rack and preventing the rack from sliding through the trigger housing in more than one direction. Actuating the trigger assembly causes an actuator protrusion on the trigger to press against the rack engagement cylinder, moving the first pawled surface of the toothed rack stop away from the rack and allowing the rack to slide freely.

20 Claims, 5 Drawing Sheets

(56) References Cited

U.S. PATENT DOCUMENTS

| | | | |
|---|---|---|---|
| 2010/0152751 A1* | 6/2010 | Meade | A61B 17/0469 606/144 |
| 2010/0249780 A1* | 9/2010 | Rolfes | A61B 90/14 606/59 |
| 2017/0119406 A1* | 5/2017 | Triplett | A61B 17/16 |
| 2017/0143383 A1* | 5/2017 | Ingalhalikar | A61B 17/7065 |
| 2017/0150956 A1* | 6/2017 | Baudouin | A61B 17/0206 |

* cited by examiner

ORTHOPEDIC TRIGGER APPARATUS

CROSS-REFERENCE TO RELATED APPLICATIONS

This application claims priority to U.S. Provisional Patent Application 62/204,189, which is hereby incorporated by reference in its entirety.

BACKGROUND OF THE INVENTION

1. Field of Invention

This invention relates to the field of surgical instruments and more specifically to orthopedic instruments.

2. Description of Related Art

Medical devices used in surgical procedures, particular those involving the spine, require both precision and ease of use. Medical devices used to grip implants must be minutely adjustable to prevent damage to the implant, while still providing enough gripping strength to hold the implant securely during implantation.

Gripping devices must also be stably locked in a given position once the implant is securely gripped, allowing the surgeon to maneuver the device more easily. If the device does not securely lock in position, the tool may tighten or loosen, potentially resulting in injury to a person or damage to the medical tool or implant. Moreover, the device must easily unlock once the implant is ready for release.

Accordingly, it is desirable to have a trigger assembly for a gripping device that is easily locked into position and unlocked during orthopedic surgery.

BRIEF SUMMARY OF THE INVENTION

The present invention is an orthopedic trigger apparatus including a rack assembly, a trigger housing assembly and a trigger assembly. The rack assembly includes a linear rack having a plurality of rack teeth and a handle pin rotatably connecting the linear rack to a first handle. The trigger housing assembly includes a trigger housing, a rack engagement cylinder slidably enclosed within the trigger housing and a spring enclosed within the trigger housing. The trigger housing has a plurality of rack apertures. A plurality of housing pins connect the trigger housing to a second handle. The rack engagement cylinder has a plurality of cylinder apertures and a toothed rack stop. A connector pin connects the rack engagement cylinder to the toothed rack stop. The first pawled surface of the toothed rack stop meshes with the plurality of rack teeth. The spring located contacts a second surface of the toothed rack stop, biasing the first pawled surface of the toothed rack stop into meshing with the plurality of rack teeth. The trigger assembly includes a trigger having an actuator protrusion and a stop protrusion. The actuator protrusion radially extends from a trigger axis of rotation a greater distance than the stop protrusion radially extends from the trigger axis of rotation. A trigger pin rotatably connects the trigger to the trigger housing.

BRIEF DESCRIPTION OF SEVERAL VIEWS OF THE DRAWING(S)

TERMS OF ART

As used herein, the term "radial" and "radially" refer to a measurement around or from a central point.

DETAILED DESCRIPTION OF THE INVENTION

Figure 1A:
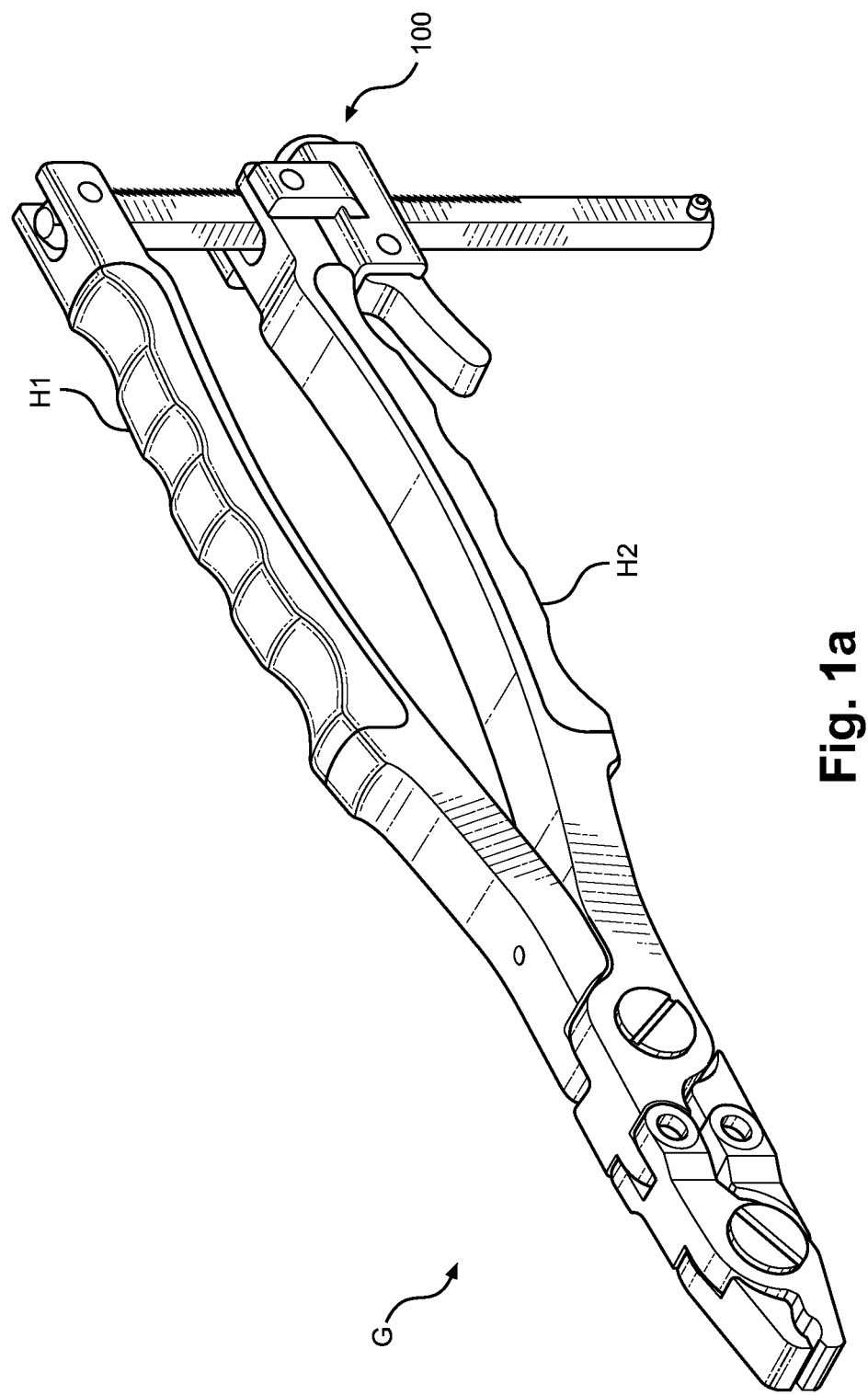
FIGS. 1a and 1b are perspective and side views, respectively, illustrating an exemplary embodiment of an orthopedic trigger apparatus attached to a rod gripper.
Figure 1B:
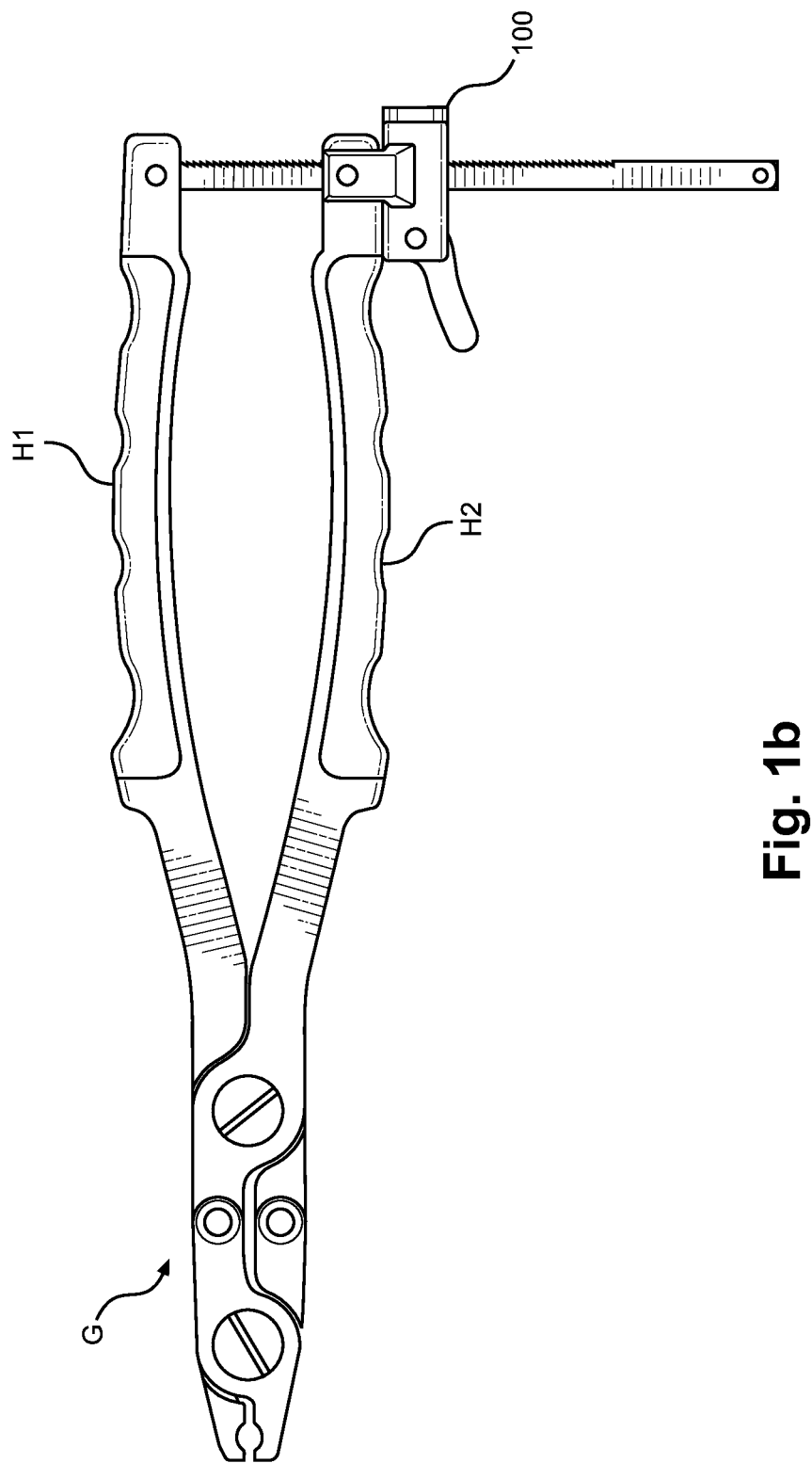

FIGS. 1a and 1b are perspective and side views, respectively, illustrating an exemplary embodiment of orthopedic trigger apparatus 100 attached to a rod gripper G having handles H1 and H2.

Figure 2:
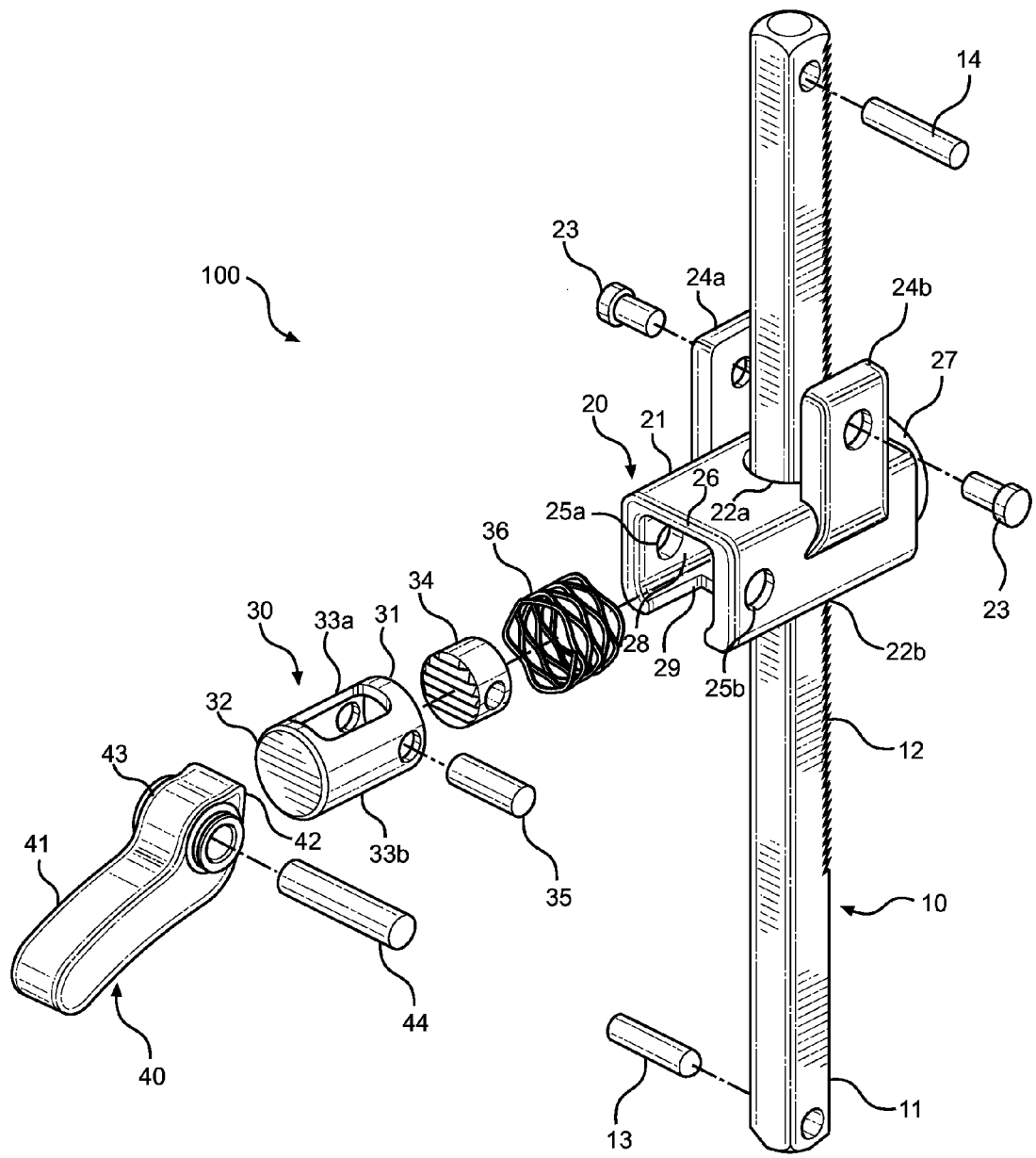
FIG. 2 is an exploded perspective view illustrating an exemplary embodiment of an orthopedic trigger apparatus.

FIG. 2 is an exploded perspective view illustrating an exemplary embodiment of orthopedic trigger apparatus 100. Orthopedic trigger apparatus 100 includes a rack assembly 10, a trigger housing assembly 20 and a trigger assembly 40. Orthopedic trigger apparatus 100 attaches to handles H1 and H2 of rod gripper G. Materials forming orthopedic trigger apparatus 100 may include, but are not limited to, stainless steel, anodized aluminum or polymers.

Rack assembly 10 includes a linear rack 11 having a plurality of rack teeth 12, a rack stop pin 13 and a handle pin 14. In the exemplary embodiment, linear rack 11 has an approximately square cross-section measuring approximately 0.184 inches to a side. Rack teeth 12 number between approximately 3 and approximately 15. Rack stop pin 13 is located at least partially within a bore at a first end of linear rack 11 and protrudes to either side of linear rack 11. When handles H1 and H2 are at maximum spread, rack stop pin 13 catches against trigger housing assembly 20 to prevent linear rack 11 from exiting trigger housing assembly 20. In the exemplary embodiment, rack stop pin 13 has a width greater than that of a plurality of rack apertures 22a and 22b. Handle pin 14 rotatably connects linear rack 11 to handle H1 at a second end of linear rack 11.

Trigger housing assembly 20 includes a trigger housing 21, housing pins 23, a rack engagement cylinder 30, a toothed rack stop 34, a connector pin 35 and a spring 36.

Trigger housing 21 is a hollow rectangular box with a height of approximately 0.317 inches to 0.323 inches. The width of trigger housing 21 may vary to accommodate wider trigger assemblies 40. Trigger housing 21 includes directly opposed rack apertures 22a and 22b on top and bottom sides, connection flanges 24a and 24b, trigger pin apertures 25a and 25b in an open housing end 26, a closed housing end 27, a cylinder channel 28 and trigger notch 29. Linear rack 11 travels through rack apertures 22a and 22b. In the exemplary embodiment, rack apertures 22a and 22b are circular apertures having a diameter of approximately 0.25 inches. Housing pins 23 connect trigger housing 21 to handle H2 through connection flanges 24a and 24b.

Rack engagement cylinder 30 is a hollow cylinder with an open cylinder end 31 and a closed cylinder end 32. Rack engagement cylinder 30 is slidably contained within cylinder channel 28 of trigger housing 21. Rack engagement cylinder 30 has directly opposed cylinder apertures 33a and 33b on upper and lower sides, respectively, through which linear rack 11 travels. Cylinder apertures 33a and 33b substantially align with rack apertures 22a and 22b. Because rack engagement cylinder 30 slides back and forth within trigger housing 21, cylinder apertures 33a and 33b are longer than rack apertures 22a and 22b. In one embodiment, each of cylinder apertures 33a and 33b is a substantially rectangular aperture measuring approximately 0.194 inches to approximately 0.198 inches wide, and approximately 0.298 inches to approximately 0.318 inches long. In the exemplary embodiment, each of cylinder apertures 33a and 33b is a substantially rectangular aperture measuring approximately 0.308 inches long and approximately 0.196 inches wide. A first closed end of rack engagement cylinder 30 interacts with trigger assembly 40, while a second open end of rack engagement cylinder 30 contains toothed rack stop 34.

Connector pin 35 connects toothed rack stop 34 to open cylinder end 31 of rack engagement cylinder 30. A first pawled surface of toothed rack stop 34 located within rack engagement cylinder 30 interacts with linear rack 11, while a second surface of toothed rack stop 34 interacts with spring 36. The first pawled surface of toothed rack stop 34 meshes with rack teeth 12, allowing linear rack 11 to travel in one direction, but preventing linear rack 11 from traveling in the reverse direction.

Spring 36 is located in closed housing end 27 and biases the first pawled surface of toothed rack stop 34 towards engagement with linear rack 11 when trigger assembly 40 is not actuated. The spring constant of spring 36 ranges from approximately 15 lbs/in to approximately 150 lbs/in, exerting a resting force of approximately 1 pound to approximately 3 pounds on linear rack 11 through toothed rack stop 34. Spring 36 has a free length ranging from approximately 0.170 inches to approximately 0.210 inches, a resting length ranging from approximately 0.129 inches to approximately 0.169 inches and a compressed length ranging from approximately 0.0975 inches to approximately 0.1375 inches. In the exemplary embodiment, spring 36 is a wave spring with a free length of approximately 0.190 inches, a resting length of approximately 0.149 inches and a compressed length of approximately 0.1175 inches.

Trigger assembly 40 includes a trigger 41 having actuator protrusion 42 and stop protrusion 43, and a trigger pin 44. Trigger 41 rotatably connects to open housing end 26 through trigger pin 44 inserted in trigger pin apertures 25a and 25b. At rest, trigger 41 abuts closed cylinder end 32 of rack engagement cylinder 30. When trigger 41 rotates around trigger pin 44, actuator protrusion 42 presses against closed cylinder end 32, moving rack engagement cylinder 30 against the bias of spring 36 and disengaging toothed rack stop 34 from linear rack 11. As trigger 41 continues to rotate, stop protrusion 43 comes into contact with an upper inner surface of trigger housing 21, preventing over-rotation of trigger 41. To prevent trigger 41 from stopping when contacting a lower inner surface of open housing end 26, trigger housing 21 may include trigger housing notch 29 in a lower inner surface of open housing end 26.

To allow trigger 41 to rotate, actuator protrusion 42 extends a greater radial distance from the trigger axis of rotation than stop protrusion 43. This distance is proportional to the length of rack teeth 12, as longer rack teeth 12 will require correspondingly greater rotation of trigger 41 to disengage rack engagement cylinder 30. Actuator protrusion 42 radially extends from the trigger axis of rotation approximately 0.018 inches to approximately 0.028 inches further than stop protrusion 43. In the exemplary embodiment, actuator protrusion 42 radially extends from the trigger axis of rotation approximately 0.021 inches further than stop protrusion 43. Actuator protrusion 42 and stop protrusion 43 are radially spaced such that during rotation actuator protrusion 42 contacts rack engagement cylinder 30 before stop protrusion 43 contacts said trigger housing 21.

Figure 3A:
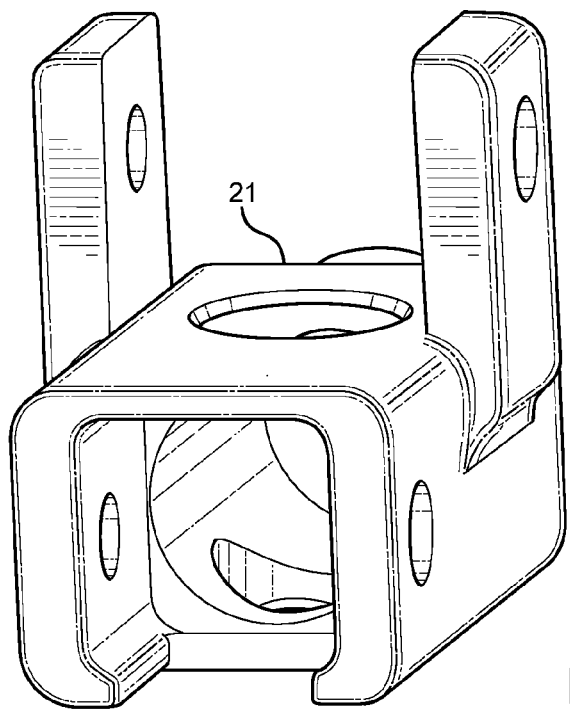
FIGS. 3a and 3b are front and side perspective views, respectively, of a trigger housing.
Figure 3B:
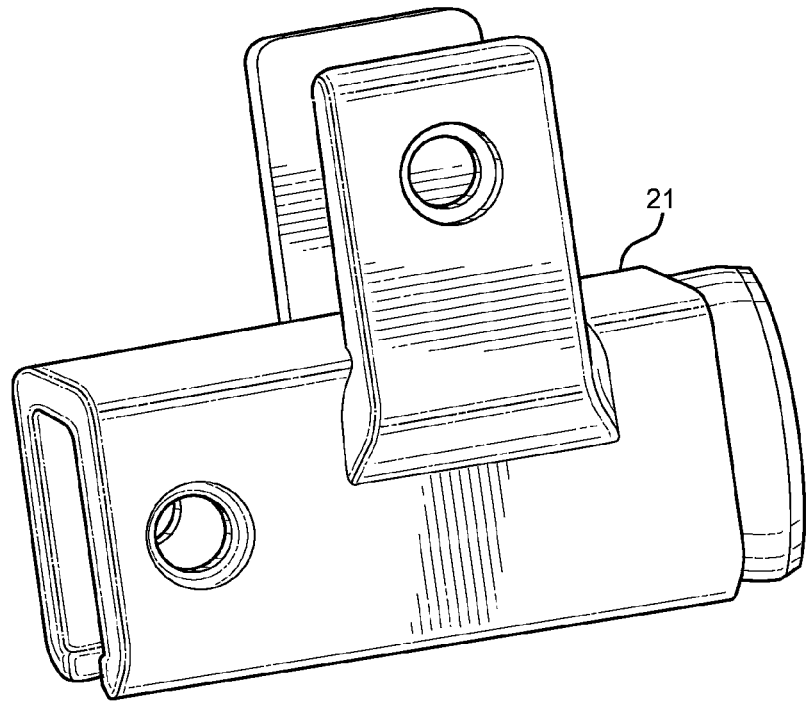

FIGS. 3a and 3b are front and side perspective views, respectively, of trigger housing 21.

Figure 4A:
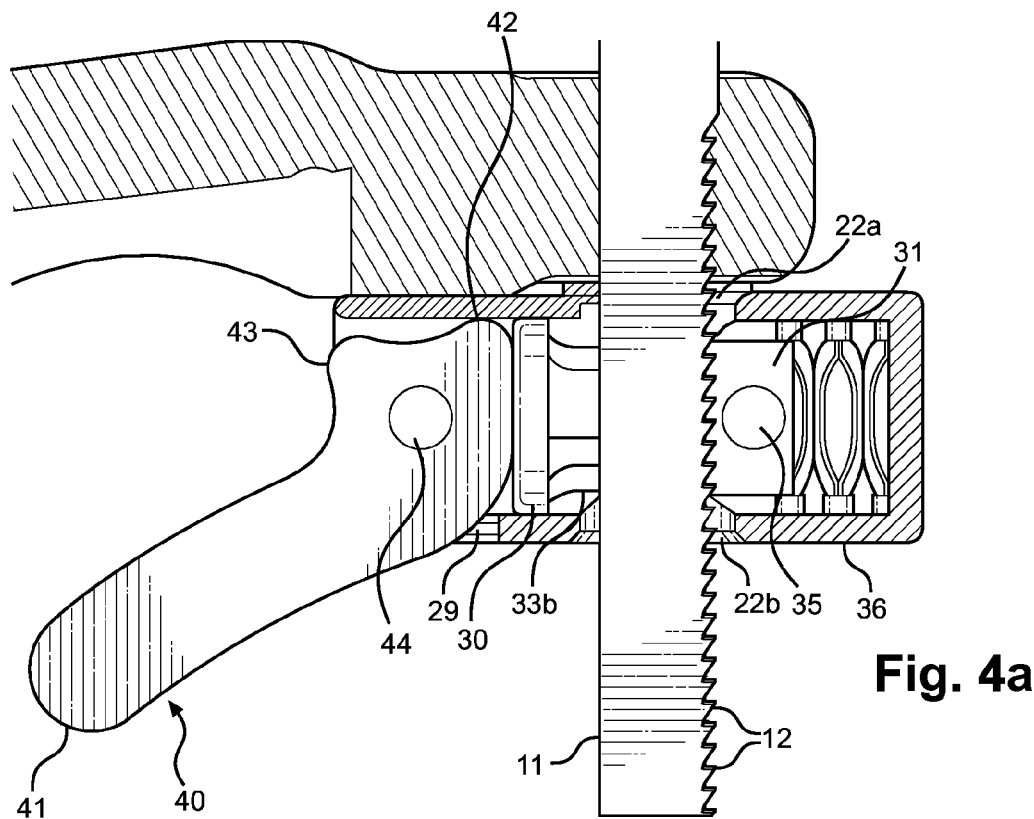
FIGS. 4a and 4b are cross-sectional views illustrating an exemplary embodiment of an orthopedic trigger apparatus in unactuated and actuated states, respectively.
Figure 4B:
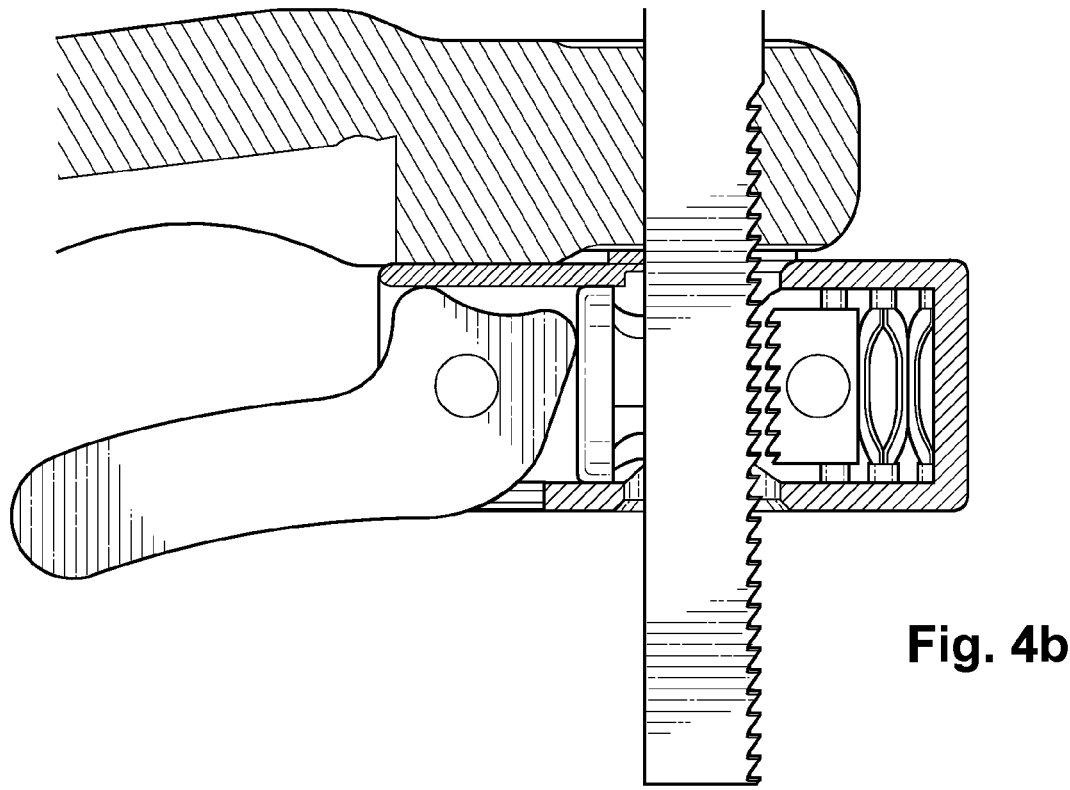

FIGS. 4a and 4b are cross-sectional views illustrating an exemplary embodiment of orthopedic trigger apparatus 100 in unactuated and actuated states, respectively.

It will be understood that many additional changes in the details, materials, procedures and arrangement of parts, which have been herein described and illustrated to explain the nature of the invention, may be made by those skilled in the art within the principle and scope of the invention as expressed in the appended claims.

It should be further understood that the drawings are not necessarily to scale; instead, emphasis has been placed upon illustrating the principles of the invention. Moreover, the terms "substantially" or "approximately" as used herein may be applied to modify any quantitative representation that could permissibly vary without resulting in a change in the basic function to which it is related.

What is claimed is:

1. An orthopedic trigger apparatus comprising:
    a rack assembly comprising:
        a linear rack having a plurality of rack teeth and
        a handle pin rotatably connecting said linear rack to a first handle;
    a trigger housing assembly comprising
        a trigger housing having a plurality of rack apertures, wherein a plurality of housing pins connect said trigger housing to a second handle,
        a rack engagement cylinder slidably enclosed within said trigger housing and having a plurality of cylinder apertures and a toothed rack stop, wherein a connector pin connects said rack engagement cylinder to said toothed rack stop, wherein a first pawled surface of said toothed rack stop meshes with said plurality of rack teeth, and
        a spring enclosed within said trigger housing and contacting a second surface of said toothed rack stop, wherein said spring biases said first pawled surface of said toothed rack stop into meshing with said plurality of rack teeth; and
    a trigger assembly comprising
        trigger having an actuator protrusion and a stop protrusion, wherein said actuator protrusion radially extends from a trigger axis of rotation a greater distance than said stop protrusion radially extends from said trigger axis of rotation, and
        a trigger pin rotatably connecting said trigger to said trigger housing.

2. The apparatus of claim 1, wherein said rack assembly further comprises a rack stop pin located at least partially within a bore at a first end of said linear rack and protruding to either side of said linear rack.

3. The apparatus of claim 2, wherein said rack stop pin has a width greater than a width of said plurality of rack apertures.

4. The apparatus of claim 3, wherein said rack stop pin has a width greater than approximately 0.25 inches.

5. The apparatus of claim 1, wherein said rack teeth number between approximately 3 and approximately 15.

6. The apparatus of claim 1, wherein said linear rack has a square cross-section measuring approximately 0.184 inches to a side.

7. The apparatus of claim 1, wherein said plurality of cylinder apertures substantially align with said plurality of rack apertures.

8. The apparatus of claim 1, wherein each of said plurality of cylinder apertures is longer than each of said plurality of rack apertures.

9. The apparatus of claim 1, wherein each of said plurality of cylinder apertures is a substantially rectangular aperture.

10. The apparatus of claim 9, wherein each of said plurality of cylinder apertures ranges in length from approximately 0.298 inches to approximately 0.318 inches, and in width from approximately 0.194 inches to approximately 0.198 inches.

11. The apparatus of claim 10, wherein each of said plurality of cylinder apertures measures approximately 0.308 inches long by approximately 0.196 inches wide.

12. The apparatus of claim 1, wherein said spring is a wave spring.

13. The apparatus of claim 1, wherein said spring has a free length ranging from approximately 0.170 inches to approximately 0.210 inches, a resting length ranging from approximately 0.129 inches to approximately 0.169 inches and a compressed length ranging from approximately 0.0975 inches to approximately 0.1375 inches.

14. The apparatus of claim 13, wherein said spring has a free length of approximately 0.190 inches, a resting length of approximately 0.149 inches and a compressed length of approximately 0.1175 inches.

15. The apparatus of claim 1, wherein a spring constant of said spring ranges from approximately 15 lbs/in to approximately 150 lbs/in.

16. The apparatus of claim 1, wherein said spring exerts a resting force of approximately 1 pound to approximately 3 pounds on said linear rack through said toothed rack stop.

17. The apparatus of claim 1, wherein said actuator protrusion and said stop protrusion are radially spaced such that during rotation said actuator protrusion contacts said rack engagement cylinder before said stop protrusion contacts said trigger housing.

18. The apparatus of claim 1, wherein an actuator protrusion extension distance is proportional to a length of said plurality of rack teeth.

19. The apparatus of claim 1, wherein said actuator protrusion radially extends from said trigger axis of rotation approximately 0.018 inches to approximately 0.028 inches further than said stop protrusion.

20. The apparatus of claim 19, wherein said actuator protrusion radially extends from said trigger axis of rotation approximately 0.021 inches further than said stop protrusion.

* * * * *